(12) United States Patent
Coulombe

(10) Patent No.: US 10,194,978 B2
(45) Date of Patent: Feb. 5, 2019

(54) SUPPORTING CATHETER FOR USE FOR PHRENIC NERVE PACING

(71) Applicant: Medtronic CryoCath LP, Toronto (CA)

(72) Inventor: Nicolas Coulombe, Anjou (CA)

(73) Assignee: Medtronic CryoCath LP, Toronto, Ontario (CA)

( * ) Notice: Subject to any disclaimer, the term of this patent is extended or adjusted under 35 U.S.C. 154(b) by 1018 days.

(21) Appl. No.: 14/304,310

(22) Filed: Jun. 13, 2014

(65) Prior Publication Data

US 2015/0359487 A1    Dec. 17, 2015

(51) Int. Cl.
*A61B 5/042* (2006.01)
*A61M 25/06* (2006.01)
(Continued)

(52) U.S. Cl.
CPC ........ *A61B 18/1492* (2013.01); *A61B 5/6856* (2013.01); *A61M 25/0662* (2013.01);
(Continued)

(58) Field of Classification Search
CPC .............. A61B 18/1492; A61B 5/6857; A61B 2010/00351; A61B 1/00154;
(Continued)

(56) References Cited

U.S. PATENT DOCUMENTS 5,573,520 A * 11/1996 Schwartz .......... A61M 25/0013
604/264
5,785,706 A * 7/1998 Bednarek .......... A61M 25/0662
600/372

(Continued)

FOREIGN PATENT DOCUMENTS

EP    1233717 B1    8/2006
EP    1296604 B1    1/2007
(Continued)

OTHER PUBLICATIONS

International Search Report and Written Opinion dated Jul. 27, 2015, for corresponding International Application No. PCT/CA2015/000330; International Filing Date: May 22, 2015 consisting of 8 pages.
(Continued)

*Primary Examiner* — Lee S Cohen
*Assistant Examiner* — Erin M Cardinal
(74) *Attorney, Agent, or Firm* — Christopher & Weisberg, P.A.

(57) ABSTRACT

A device, system, and method for providing support to a mapping catheter during mapping or pacing and for adjusting the diameter of a distal loop portion of currently available mapping catheters. A medical device support device includes an elongate body defining a wall and an at least substantially linear proximal portion and a distal portion being transitionable between an at least substantially linear configuration and an expanded configuration, the elongate body defining a lumen extending through the proximal portion and distal portion, the lumen being entirely surrounded by the wall in the proximal portion and being partially surrounded by the wall in the distal portion. For example, the lumen may be sized to receive a mapping catheter therein such that adjustment of the configuration or diameter of the distal portion of the elongate body will likewise modify the configuration or diameter of the distal portion of the mapping catheter.

17 Claims, 14 Drawing Sheets

(51) Int. Cl.
- *A61B 18/14* (2006.01)
- *A61B 5/00* (2006.01)
- *A61B 18/00* (2006.01)
- *A61B 18/02* (2006.01)
- *A61B 18/18* (2006.01)
- *A61M 25/00* (2006.01)

(52) U.S. Cl.
CPC ......... *A61B 5/0422* (2013.01); *A61B 5/4836* (2013.01); *A61B 5/6857* (2013.01); *A61B 2018/0022* (2013.01); *A61B 2018/00351* (2013.01); *A61B 2018/00577* (2013.01); *A61B 2018/00583* (2013.01); *A61B 2018/00642* (2013.01); *A61B 2018/00839* (2013.01); *A61B 2018/00994* (2013.01); *A61B 2018/0212* (2013.01); *A61B 2018/0262* (2013.01); *A61B 2018/1861* (2013.01); *A61M 2025/0006* (2013.01); *A61M 2025/0681* (2013.01)

(58) Field of Classification Search
CPC .... A61B 5/6856; A61N 1/048; A61N 1/0488; A61N 1/05–1/0563; A61N 1/086; A61M 25/0622; A61M 2025/0004; A61M 2025/0006; A61M 2025/0681
See application file for complete search history.

(56) References Cited

U.S. PATENT DOCUMENTS

| | | | | |
|---|---|---|---|---|
| 5,919,188 | A * | 7/1999 | Shearon | A61B 18/1492 600/374 |
| 5,993,462 | A * | 11/1999 | Pomeranz | A61B 18/1492 600/508 |
| 6,010,500 | A * | 1/2000 | Sherman | A61B 18/1492 606/41 |
| 6,071,279 | A * | 6/2000 | Whayne | A61B 18/1492 606/41 |
| 6,402,746 | B1 * | 6/2002 | Whayne | A61B 18/1492 128/898 |
| 6,440,128 | B1 | 8/2002 | Edwards et al. | |
| 7,033,352 | B1 * | 4/2006 | Gauthier | A61B 18/1492 606/33 |
| 7,077,842 | B1 | 7/2006 | Cosman | |
| 7,285,119 | B2 | 10/2007 | Stewart et al. | |
| 2002/0183817 | A1 * | 12/2002 | Van Venrooij | A61N 1/0534 607/116 |
| 2004/0097965 | A1 * | 5/2004 | Gardeski | A61M 25/0021 606/129 |
| 2004/0106918 | A1 * | 6/2004 | Cox | A61B 17/00234 606/41 |
| 2004/0199154 | A1 | 10/2004 | Nahon et al. | |
| 2004/0243118 | A1 | 12/2004 | Ayers et al. | |
| 2005/0131343 | A1 * | 6/2005 | Abrams | A61M 25/0662 604/95.04 |
| 2005/0159799 | A1 * | 7/2005 | Daglow | A61N 1/0551 607/116 |
| 2006/0241366 | A1 | 10/2006 | Falwell et al. | |
| 2006/0287650 | A1 * | 12/2006 | Cao | A61B 18/1492 606/41 |
| 2006/0293646 | A1 * | 12/2006 | Whayne | A61B 18/148 606/27 |
| 2009/0024091 | A1 | 1/2009 | Li et al. | |
| 2010/0168827 | A1 * | 7/2010 | Schultz | A61M 25/0136 607/116 |
| 2012/0316417 | A1 * | 12/2012 | Vetter | A61N 1/0534 600/377 |
| 2013/0304062 | A1 | 11/2013 | Chan et al. | |
| 2014/0012251 | A1 | 1/2014 | Himmelstein et al. | |
| 2014/0052097 | A1 | 2/2014 | Petersen et al. | |

FOREIGN PATENT DOCUMENTS

| | | |
|---|---|---|
| WO | 9320769 A1 | 10/1993 |
| WO | 2006010908 A1 | 2/2006 |
| WO | 2009140067 A1 | 11/2009 |
| WO | 2011019838 A2 | 2/2011 |
| WO | 2012078612 A2 | 6/2012 |

OTHER PUBLICATIONS

Supplementary European Search Report for Application No. EP 15806473 dated Feb. 8, 2018.

* cited by examiner

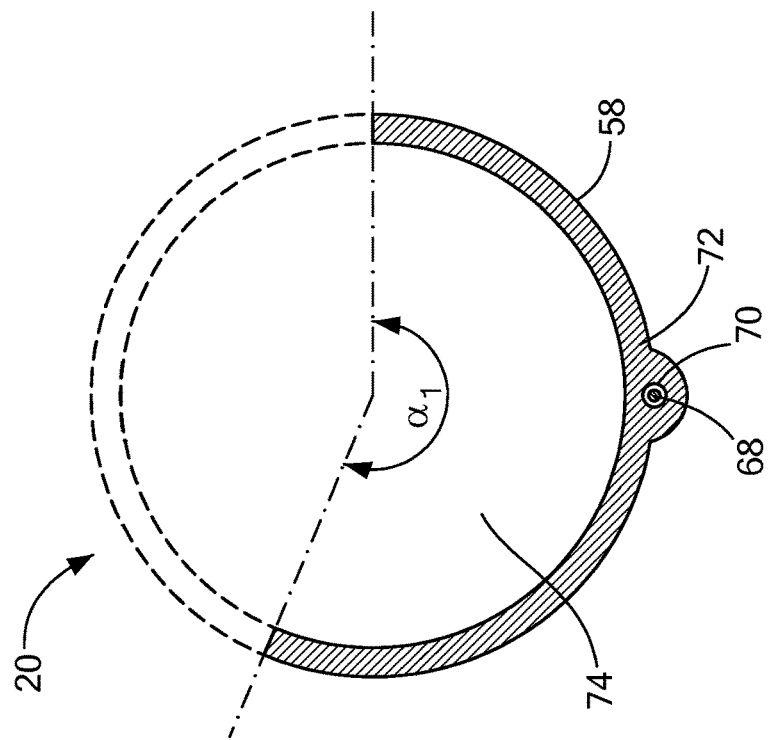
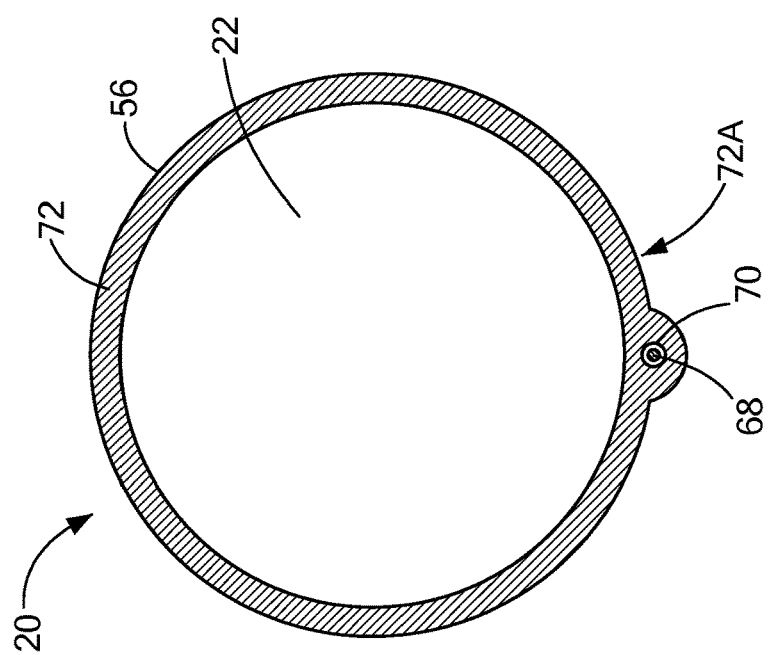

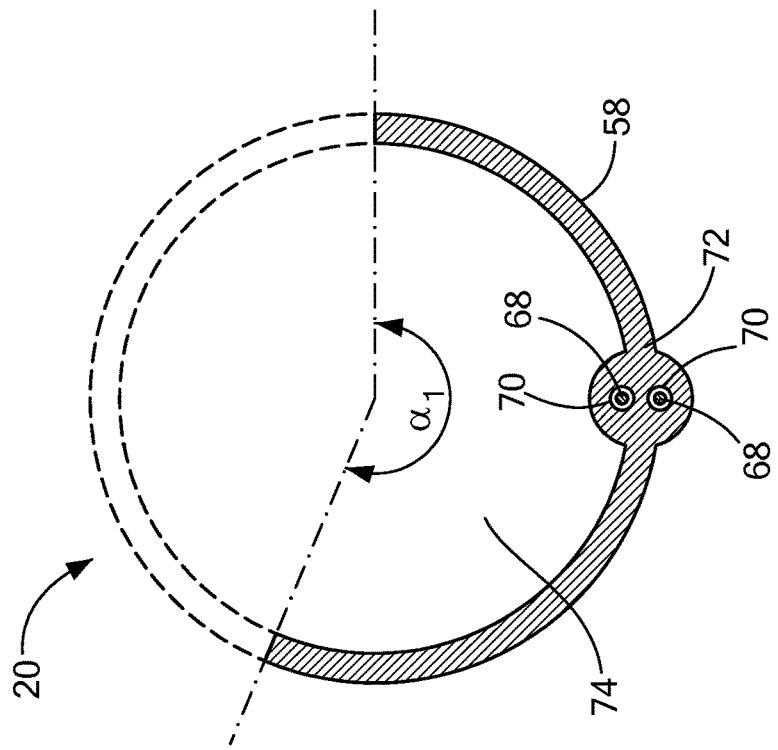
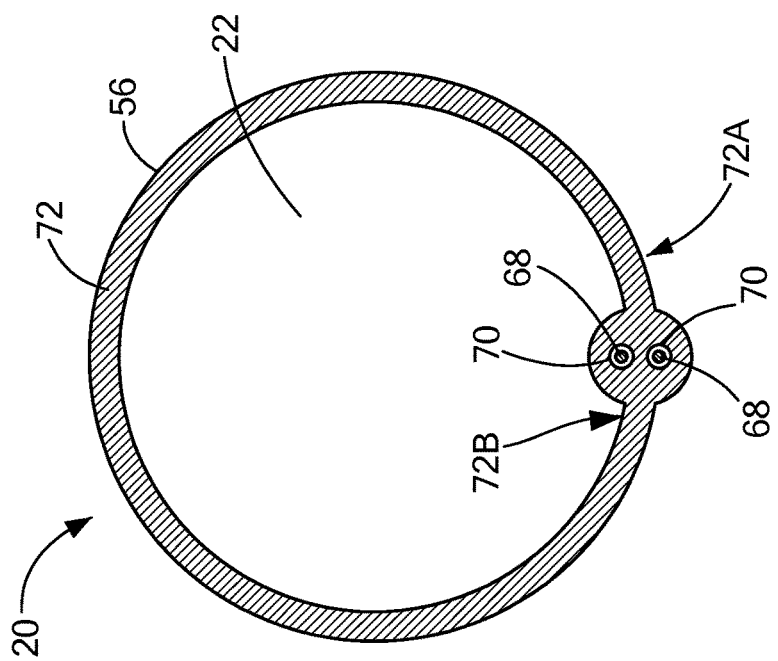
FIG. 3D
FIG. 3C

SUPPORTING CATHETER FOR USE FOR PHRENIC NERVE PACING

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention advantageously provides a device, system, and method for providing support to a mapping catheter during, for example, when the mapping catheter is used for electrophysiology or pacing procedures. The present invention also advantageously provides a device, system, and method for adjusting the diameter of a distal loop portion of currently available mapping catheters.

BACKGROUND OF THE INVENTION

Cryoablation, or killing tissue with low temperatures, is often used to treat cardiac arrhythmia conditions such as atrial fibrillation. However, when treating particular regions of tissue, through thermal energy interaction or the like for example, it may be difficult to direct or control the depth and intensity of the heat transfer. The delivery of thermal energy or other therapeutic modality, such as radiofrequency or cryogenic applications, may not necessarily be contained to the exact region or depth desired for treatment, as the tissue may have varying therapy-conducive properties affected by the surrounding physiological environment. While thermal control or precision may be of more concern with certain treatment modalities, such as radiofrequency, microwave, and/or cryogenic treatment procedures, it is often desirable to limit thermal treatment or exposure to just the tissue desired. Failure to do so may otherwise negatively and adversely affect surrounding tissue structures or organs that are sensitive and susceptible to undesired damage.

For example, when attempting to treat cardiac tissue, there are many nearby sensitive tissue structures that may react adversely to thermal applications. In particular, when thermally treating or ablating tissue in or about the heart, it is essential that critical physiological structures such as the phrenic nerve, sinoatrial node, and the like are not inadvertently destroyed through such ablation therapy. The phrenic nerve is made up mostly of motor nerve fibers that produce contractions of the diaphragm and thus affect breathing and respiration patterns and conditions. In addition, the phrenic nerve provides sensory innervation for many components of the mediastinum and pleura, as well as the upper abdomen, especially the liver, and the gall bladder.

The phrenic nerve is generally referred to in two segments: the right and left phrenic nerves. Both phrenic nerves run from C3, C4 and C5 vertebrae along the anterior scalene muscle deep to the carotid sheath. The right phrenic nerve passes over the brachiocephalic artery, posterior to the subclavian vein, and then crosses the root of the right lung anteriorly and then leaves the thorax by passing through the vena cava hiatus opening in the diaphragm at the level of T8. The right phrenic nerve passes over the right atrium, proximate the superior vena cava (SVC). The left phrenic nerve passes over the pericardium of the left ventricle and pierces the diaphragm separately.

The right atrium and left atrium of the heart may be the location or origin of arrhythmias or other physiological maladies and thus targeted for tissue ablation in order to remove or otherwise remedy the abnormal electrophysiological occurrence. In thermally treating or ablating select cardiac regions, the phrenic nerve may be at risk of being similarly, although unintentionally, ablated. This could severely impact the normal respiratory functioning of the patient. Such injury can manifest as a transient phrenic functional block, transient phrenic nerve palsy (PNP), or longer-term phrenic nerve injury. These injuries reduce respiratory function and can require many weeks or months to resolve. In the worst cases, this reduced function requires mechanical ventilation assistance to maintain respiration. As such, the risk of such unintentional and undesirable destruction or application of thermal energy to this and other cursory structures compels a desire to monitor or otherwise detect potentially-damaging consequences during treatment.

Such monitoring is typically performed using pacing the phrenic nerve and using continuous fluoroscopy during the ablation to visualize a consistent diaphragmatic response, or palpation of the abdomen to confirm diaphragmatic movement. Both methods require vigilance on the part of the operator, and can distract the physician from the main focus of the diagnostic or treatment procedure at hand. Further, in the case of fluoroscopic monitoring, the patient is exposed to increased x-ray radiation.

Phrenic nerve palsy, which may cause hemidiaphragm paralysis, is the most encountered complication of cryoablation for atrial fibrillation. Various techniques have been developed to monitor the phrenic nerve, but all revolve around delivering pacing energy to the phrenic nerve from within the SVC, at a convenient location proximate a portion of the phrenic nerve, such as the left phrenic nerve. Typically, a focal catheter is used to stimulate, or pace, the phrenic nerve, but the catheter often shifts during the procedure, resulting in loss of capture. To the physician, this may appear as though the diaphragm has stopped contracting, and the physician may decide to prematurely stop the ablation procedure.

Known mapping catheters, such as the ACHIEVE® mapping catheter (Medtronic, Inc., Minneapolis, Minn.), may have a distal portion that is expandable to bring one or more electrodes in contact with target tissue, such as an inner circumference of a pulmonary vein. Such a device may be suited for phrenic nerve monitoring, but the expanded distal portion may have an outer diameter that is too small to bring the electrodes in contact with an inner diameter of the SVC, which may be larger than that of a pulmonary vein. Further, currently known mapping catheters may lack the stiffness or strength to be used without, for example, a cryoballoon device.

Accordingly, it is desirable to provide a device and system for monitoring the phrenic nerve from within the SVC that is more stable than currently known mapping catheters, and that includes an expandable distal portion that is adjustable to ensure contact between electrodes and target tissue in any of a variety of vessel sizes.

SUMMARY OF THE INVENTION

The present invention advantageously provides a device, system, and method for providing support to a mapping catheter during, for example, when the mapping catheter is used for electrophysiology or pacing procedures. The present invention also advantageously provides a device, system, and method for adjusting the diameter of a distal loop portion of currently available mapping catheters. In one embodiment, a medical device support device may include an elongate body defining a wall and including an at least substantially linear proximal portion and a distal portion being transitionable between a first at least substantially linear configuration and a second expanded configuration, the elongate body defining a lumen extending through the proximal portion and distal portion, the lumen being entirely surrounded by the wall in the proximal portion of the elongate body and being partially surrounded by the wall in the distal portion of the elongate body. For example, the lumen may be sized to receive a mapping catheter therein. The distal portion of the elongate body may define arcuate configuration when in the second expanded configuration. The proximal portion of the elongate body may define a longitudinal axis and the distal portion of the elongate body may lie in a plane that is substantially orthogonal to the longitudinal axis when the distal portion is in the second expanded configuration. The proximal portion of the elongate body may be composed of a first material having a first durometer and the distal portion of the elongate body may be composed of a second material having a second durometer, the first durometer being greater than the second durometer. Further, the distal portion of the elongate body in the second expanded configuration may have an adjustable outer diameter. For example, the distal portion of the elongate body in the second expanded configuration may be transitionable between a first minimum outer diameter and a second maximum outer diameter. The support device may further include one or more actuator wires each being disposed within an enclosed channel defined by the elongate body wall. The outer diameter of the distal portion of the elongate body in the second expanded configuration may be adjusted by manipulating the one or more actuator wires. As a non-limiting example, manipulating the one or more actuator wires may include at least one of heating the one or more actuator wires to a temperature greater than a predetermined transformation temperature and exerting a pull force on the one or more actuator wires.

In one embodiment, a support device sized to be used with a mapping catheter may include an elongate body defining a wall and including an at least substantially linear proximal portion defining a longitudinal axis and a distal portion being transitionable between a first at least substantially linear configuration and a second expanded configuration, the elongate body defining a lumen extending through the proximal portion and distal portion, the lumen being entirely surrounded by the wall in the proximal portion of the elongate body and being partially surrounded by the wall in the distal portion of the elongate body, and the distal portion of the elongate body in the second expanded configuration having an adjustable diameter that is transitionable between a first outer diameter and a second outer diameter. The distal portion of the elongate body may lie in a plane that is substantially orthogonal to the longitudinal axis of the proximal portion of the elongate body when the distal portion of the elongate body is in the second expanded configuration. The proximal portion of the elongate body may be composed of a first material having a first durometer and the distal portion of the elongate body may be composed of a second material having a second durometer, the first durometer being greater than the second durometer.

In one embodiment, a system for monitoring a nerve proximate an ablation site may include a support device defining a wall and including an at least substantially linear proximal portion and a distal portion being transitionable between a first at least substantially linear configuration and a second arcuate configuration, the support device defining a lumen extending through the proximal portion and distal portion, the lumen being entirely surrounded by the wall in the proximal portion of the support device and being partially surrounded by the wall in the distal portion of the support device such that the wall defines an opening in the distal portion of the support device; and a mapping catheter within the lumen of the elongate body, the mapping catheter having an at least substantially linear proximal portion and a distal portion being transitionable between a first at least substantially linear configuration and a second arcuate configuration, the mapping catheter including one or more electrodes on the distal portion. The proximal portion of the mapping catheter may be disposed within the lumen in the proximal portion of the support device and the distal portion of the mapping catheter may be disposed within the lumen in the distal portion of the support device. At least a portion of each of the one or more electrodes on the distal portion of the mapping catheter may be exposed through the opening in the wall in the distal portion of the support device. The distal portion of the support device in the second arcuate configuration may have an adjustable diameter that is transitionable between a first outer diameter and a second outer diameter. The system may further include an energy source in electrical communication with the one or more electrodes of the mapping catheter and one or more actuator wires. The one or more actuator wires may also be in communication with the energy source, and the distal portion of the support device may be transitioned between the first and second outer diameters when an electrical current from the energy source is transmitted through the one or more actuator wires.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 3A shows a first cross-sectional view of a proximal portion of a support device;

FIG. 3B shows a first cross-sectional view of a distal portion of a support device;

FIG. 3C shows a second cross-sectional view of a proximal portion of a support device;

FIG. 3D shows a second cross-sectional view of a distal portion of a support device;

DETAILED DESCRIPTION OF THE INVENTION

Figure 1:
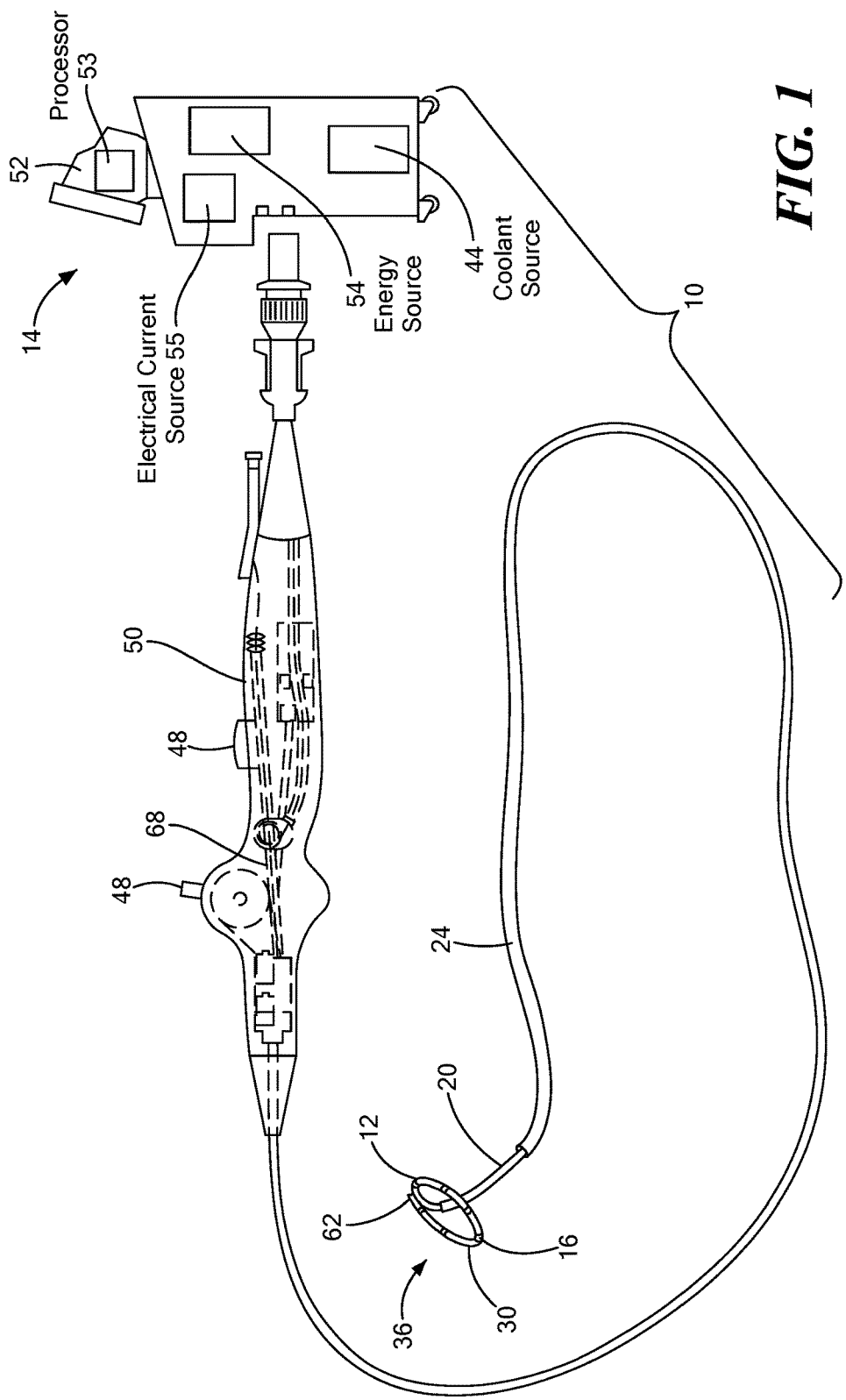
FIG. 1 shows an exemplary medical system including a mapping catheter and a support device.
Figure 2:
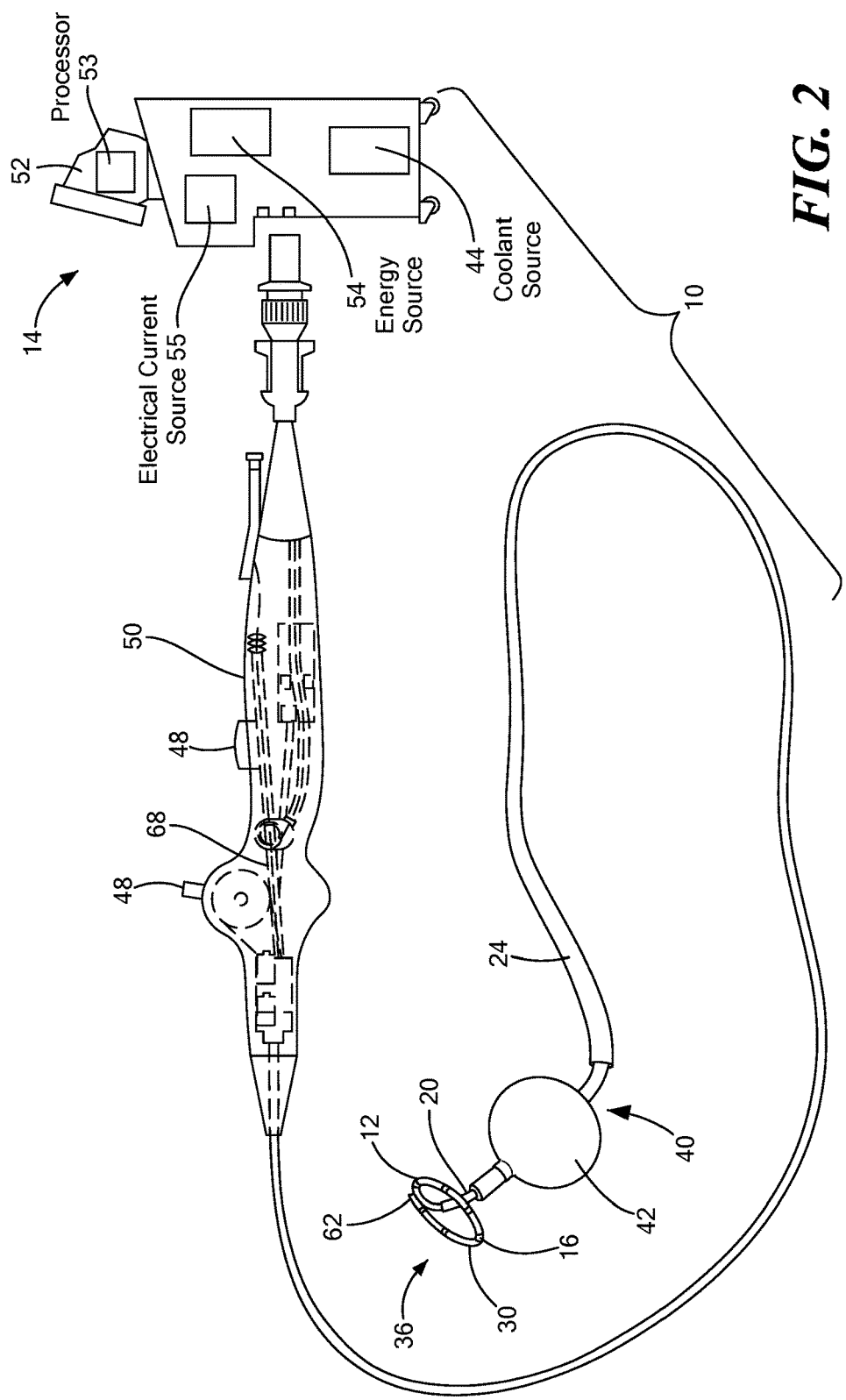
FIG. 2 shows an exemplary medical system including a mapping catheter, a support device, and a thermal treatment device.

The present invention advantageously provides a device, system, and method for providing support to a mapping catheter during, for example, when the mapping catheter is used for electrophysiology or pacing procedures. The present invention also advantageously provides a device, system, and method for forming and/or adjusting the diameter of a distal loop portion of currently available mapping catheters. Referring now to the drawing figures in which like reference designations refer to like elements, an embodiment of a medical system including a support device in accordance with principles of the present invention is shown in FIGS. 1 and 2 and generally designated as "10." The system 10 generally includes a medical device 12 that may be coupled to a control unit 14 or operating console. The medical device 12 may be configured to interact with tissue, such as with one or more electrodes 16. For example, the medical device 12 may be a mapping and/or pacing catheter that is configured to record electrical signals from cardiac tissue, stimulate tissue during a cardiac pacing procedure, and/or thermally treat tissue. Although the device 12 may be used for mapping, pacing, and/or thermal treatment, the device 12 may be referred to herein as a "mapping catheter" for simplicity.

The system 10 may also include a support device 20 having a lumen 22 therein. The support device 20 may be removably insertable into a sheath 24 or other guide element for delivery, for example, through a patient's vasculature, to a target location. Further, the support device 20 may be movably (for example, longitudinally slidably) and/or rotatably disposed within the sheath 24, such that the sheath 24 and support device 20 are movable independently of each other. The mapping catheter 12 may be removably insertable into the lumen 22 of the support device 20. However, as shown and described in greater detail in FIGS. 6-7B, the distal portion 30 of the mapping catheter, including the distal tip 32, may be removably engageable with at least a portion of the support device 23, such that the mapping catheter 12 and the support device 20 cannot be moved independently of each other, and are instead steered, advanced through the sheath 24, and expanded from a first delivery configuration within the sheath 24 to a second expanded configuration external to the sheath 24 together as a unit. This mapping catheter 12/support device 20 unit may be referred to herein as a "supported mapping assembly 36." It will be understood that the supported mapping assembly 36 may also be used to pace and/or thermally treat tissue in addition to mapping tissue.

The system 10 of FIG. 1 is shown with a mapping catheter 12 and support device 20. The system 10 of FIG. 2 may additionally include a treatment device, such as a treatment catheter 40. As a non-limiting example, the treatment catheter 40 may include a cryoballoon 42 that is in fluid communication with a source of coolant 44. Additionally or alternatively, the treatment catheter 40 may include a balloon 42 that has one or more electrodes and is configured to deliver one or more energy modalities, such as radiofrequency, ultrasound, microwave energy, or the like. Additionally or alternatively, the treatment catheter 40 may include an expandable cage, mesh, basket, or other expandable element other than a balloon 42. The catheter 40 may also include a lumen through which the support device 20 may be removably insertable. The catheter 40, in turn, may be removably insertable within a sheath 24 for delivery to a target treatment site.

The mapping catheter 12, support device 20, and/or sheath 24 may be in communication with one or more control mechanisms 48 for steering and expanding the devices 12, 20 and sheath 24. For example, the devices 12, 20 and/or sheath 24 may be in electrical and/or mechanical communication with a handle 50, as shown in FIGS. 1 and 2. Alternatively, each device 12, 20 and sheath 24 may be in communication with its own handle. Further, each device 12, 20 may be in electrical communication with a control unit 14 that includes one or more computers 52 having one or more processors 53 that receive, process, store, and/or communicate to a user (for example, show data on a visual display and/or generate visual or audible alerts) one or more signals from the mapping catheter 12. Depending on the energy modality used, the control unit 14 may also include an energy source 54 (for example, a radiofrequency energy source), an electrical current source 55, and, optionally, a coolant source 44 that are in communication with the mapping catheter 12 and/or, if used, a treatment catheter 40.

Referring now to FIGS. 3A-7B, the support device 20 is shown in greater detail. The support device 20 may include an elongate body that includes a first or proximal at least substantially linear portion 56. The proximal portion 56 may be sized and shaped such that it may pass through a lumen of the sheath 24 or a treatment catheter 40. The proximal portion 56 may be composed of a polymer, such as a biocompatible copolymer (for example, PEBAX®) or a polymer/barium sulfate blend.

Figure 4A:
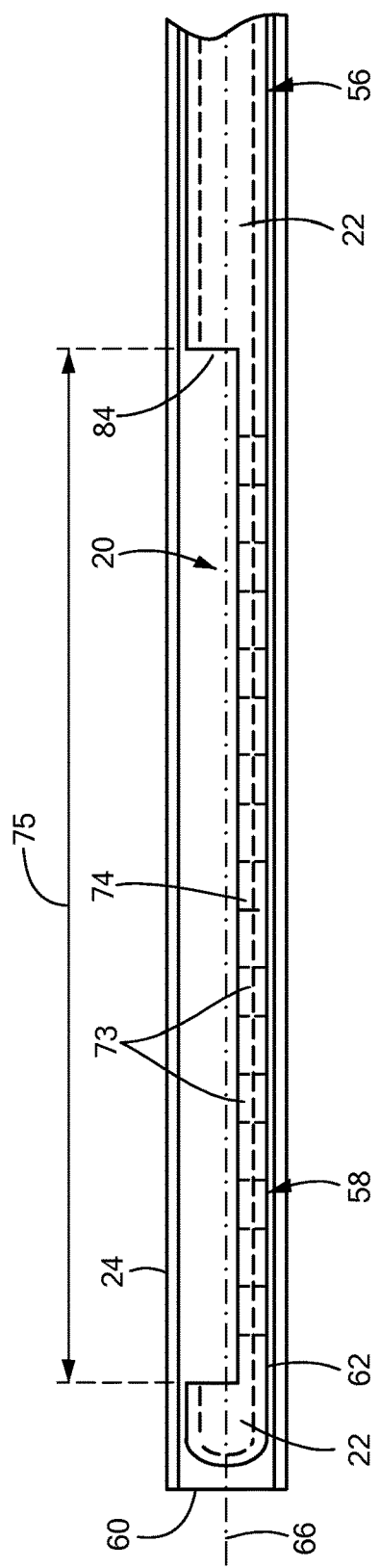
FIG. 4A shows a partially cross-sectional view of a support device within a sheath, the support device being in a delivery configuration.
Figure 4B:
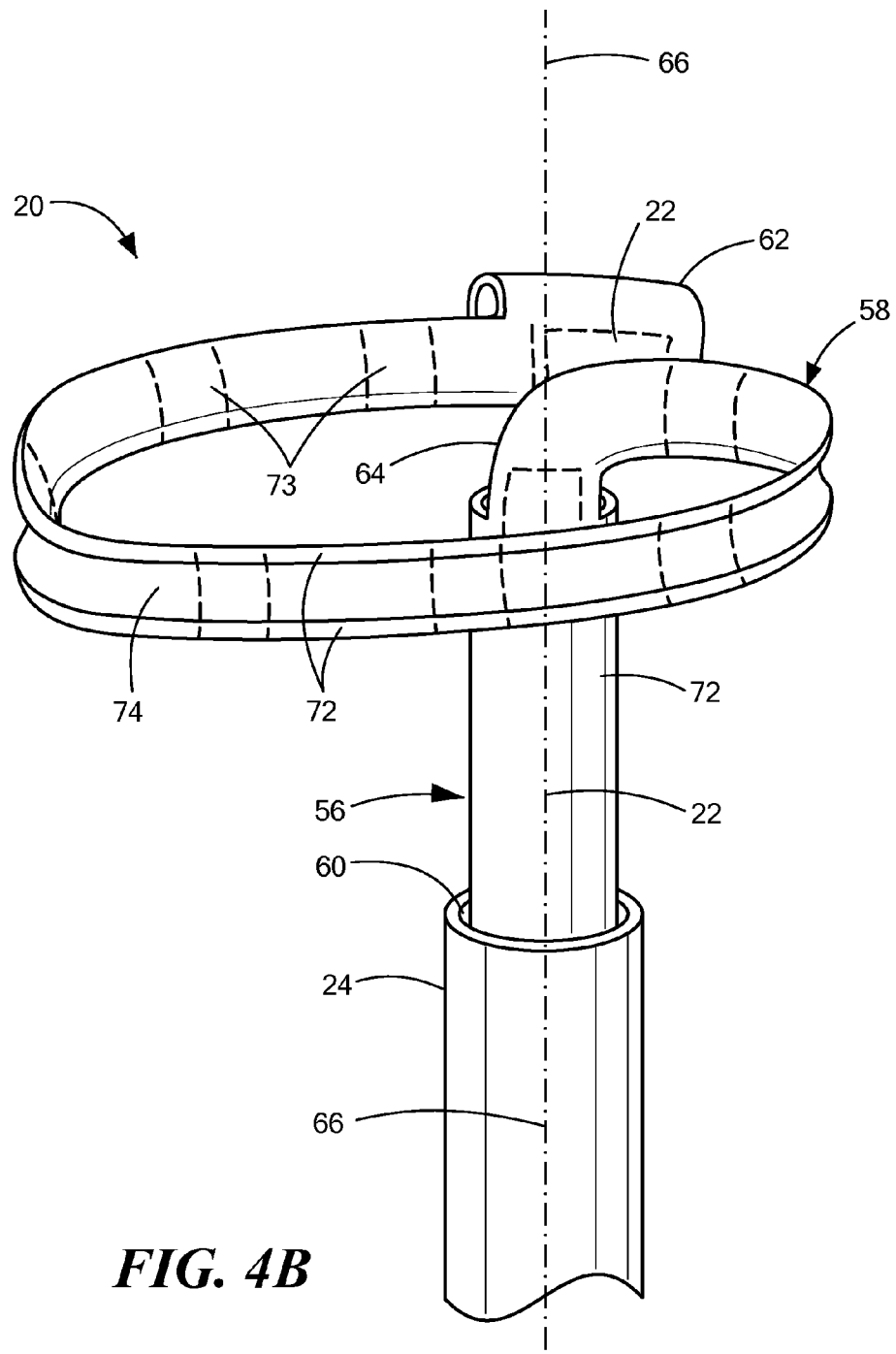
FIG. 4B shows a support device within a sheath, the support device being in an expanded configuration.
Figure 5:
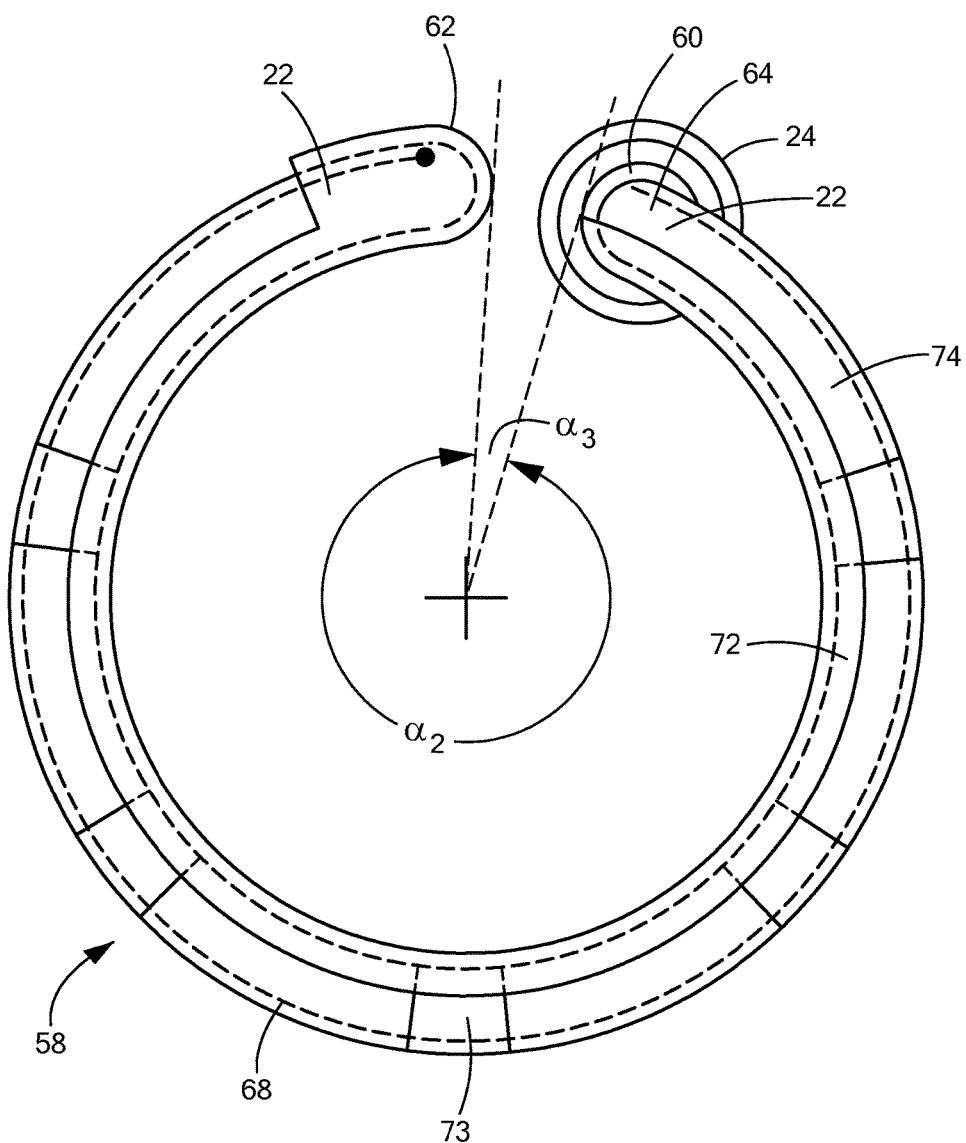
FIG. 5 shows a front view of a support device in a second expanded configuration.

The support device 20 elongate body may also include a second or distal portion 58 that is transitionable between a first at least substantially linear configuration that is like that of the proximal portion 56 (for example, as shown in FIG. 4A), and a second expanded configuration (for example, as shown in FIG. 4B). For example, the support device 20 may be advanced through a sheath 24 in a proximal-to-distal direction. As the distal portion 58 of the support device 20 exits the distal opening 60 of the sheath 24, the distal portion 58 may transition from the first at least substantially linear configuration to the second expanded configuration. As shown in FIGS. 4B-7B, the distal portion 58 may assume an arcuate shape. As a non-limiting example, the distal portion 58 may assume an arcuate shape that defines a circumference of approximately 360°±approximately 45° (shown as angle $\alpha_2$ in FIG. 5). That is, the distal tip 62 of the support device may be within approximately 0°±approximately 45° from the starting point 64 of the arcuate portion (shown as angle $\alpha_3$ in FIG. 5). Further, when in the second arcuate or expanded configuration, the distal portion 58 of the support device 20 may lie in a plane that is substantially orthogonal to the longitudinal axis 66 of the first portion 56 (as shown in FIG. 4B). When the distal portion 58 of the support device 20 is in the first at least substantially linear configuration, the proximal portion 56 and the distal portion 58 may have the same longitudinal axis 66 (for example, as shown in FIG. 4A).

As shown, for example, in FIGS. 3A-3D, the support device 20 may include one or more actuator wires 68 each located within an enclosed channel 70 in the wall 72 of the support device 20. The wall 72 may define or contain one or more channels 70 without including any areas of increased thickness. On the other hand, as shown in FIGS. 3A and 3B, one or more channels 70 may be located in an outer portion 72A of the wall 72 (that is, proximate an outer circumference of the wall 72). The wall 72 may define or contain one or more channels 70 within an area of increased wall thickness on an outer portion 72A of the wall 72 (as shown in FIGS. 3A and 3B). Actuating an actuator wire 68 (for example, exerting a pull force on the actuator wire 68, or causing the actuator wire 68 to contract) that is disposed on an outer portion 72A of the wall may allow a user to increase the diameter of the distal portion 58 of the support device 20, as shown and described in greater detail in FIGS. 7A-7C. Additionally or alternatively, one or more channels 70 may be located in an inner portion 72B of the wall 72 (that is, proximate an inner circumference of the wall 72). The wall 72 may define or contain one or more channels 70 within an area of increased wall thickness on an inner portion 72B of the wall 72 (as shown in FIGS. 3C and 3D). A distal portion of each actuator wire 58 may be attached to (such as bonded, adhered, soldered, affixed, or otherwise coupled to), for example, an inner surface of the support device distal tip 62. A proximal portion of each actuator wire 58 may be in mechanical communication with a steering mechanism 48 within the handle 50 for the manual control of the wire 68. Further, each actuator wire may be in communication with the one or more processors 53 for the automatic or semi-automatic control of the wire 68 by the system 10. Actuating an actuator wire 68 (for example, exerting a pull force on the actuator wire 68, or causing the actuator wire 68 to contract), that is disposed on an inner portion 72B of the wall may allow a user to decrease the diameter of the distal portion 58 of the support device, as shown and described in greater detail in FIGS. 7A-7C. Further, the support device 20 may include one or more channels 70 located in both an inner portion 72A and an outer portion 72B of the wall (as shown in FIGS. 3C and 3D). It will be understood that any number of channels 70 and actuator wires 68 may be used, and they may be located on an inner portion 72A, an outer portion 72B, or both. Further, the distal portion of each actuator wire 58 may be attached to the support device 20 in a location other than the tip of the distal tip 62, depending on the configuration of the distal portion 58 of the support device 20.

The distal portion 58 may be composed of the same material as the proximal portion 56. Alternatively, the distal portion 58 may be composed of a material, such as a polymer, having a higher durometer than the proximal portion 56 material. Additionally or alternatively, the distal portion 58 may include metallic inserts or rings 73 that increases the rigidity of the distal portion 58. For example, the inserts or rings 73 may be composed of Nitinol. Alternatively, the entire distal portion 58 may be composed of a shape-memory material, such as metal alloys and polymers, that transitions from the first to the second configuration in response to a temperature change. For example, the distal portion 58 may be composed of a material that has an at least substantially linear configuration at room temperature, and that has the arcuate expanded configuration at increased temperatures, such as at the temperature of the surrounding blood and/or tissue when used in a medical procedure within a patient's body. Alternatively, the distal portion 58 when in the expanded configuration may have a first outer diameter at a first temperature and a second outer diameter at a second temperature.

Alternatively, the distal portion 58 may be composed of a material that is transitionable between a first configuration and a second configuration when an electrical current is passed through the distal portion 58. For example, electrical energy transmitted to the one or more electrodes may cause an increase in the temperature of the distal portion 58 to or beyond a transformation temperature. This heat may cause the distal portion 58 to transition from an at least substantially linear configuration to an arcuate expanded and/or may cause a change in the outer diameter of the distal portion 58 when in the expanded configuration. Additionally or alternatively, as discussed in greater detail below, the configuration and/or diameter of the distal portion 58 may be adjusted using one or more actuator wires 68.

As discussed above, the proximal portion 56 of the support 20 defines a closed lumen 22 that is completely surrounded by the wall 72 of the device. The distal portion 58 of the support device 20, on the other hand, may include an "exposed" lumen 74 along at least a portion of the distal portion 58. As used herein, the term "exposed lumen" may refer to a portion of device lumen wherein the lumen is only partially surrounded by a wall 72 of the device, leaving an opening 75 in the wall 72 (for example, as shown in FIGS. 4A). As discussed below, this exposed lumen 74 may allow one or more electrodes 16 of the mapping device 12 to remain exposed and able to contact tissue. In contrast, the distal tip 62 of the support device 20 may define a closed lumen 22 that is completely surrounded by a wall 72 of the device. As a non-limiting example, the closed lumen 22 may be surrounded by the wall 72 about 360° of the circumference closed lumen 22 and the exposed lumen 74 may be surrounded by the wall about between approximately 150° and approximately 270° (shown as angle $\alpha_1$ in FIG. 3B).

Figure 6:
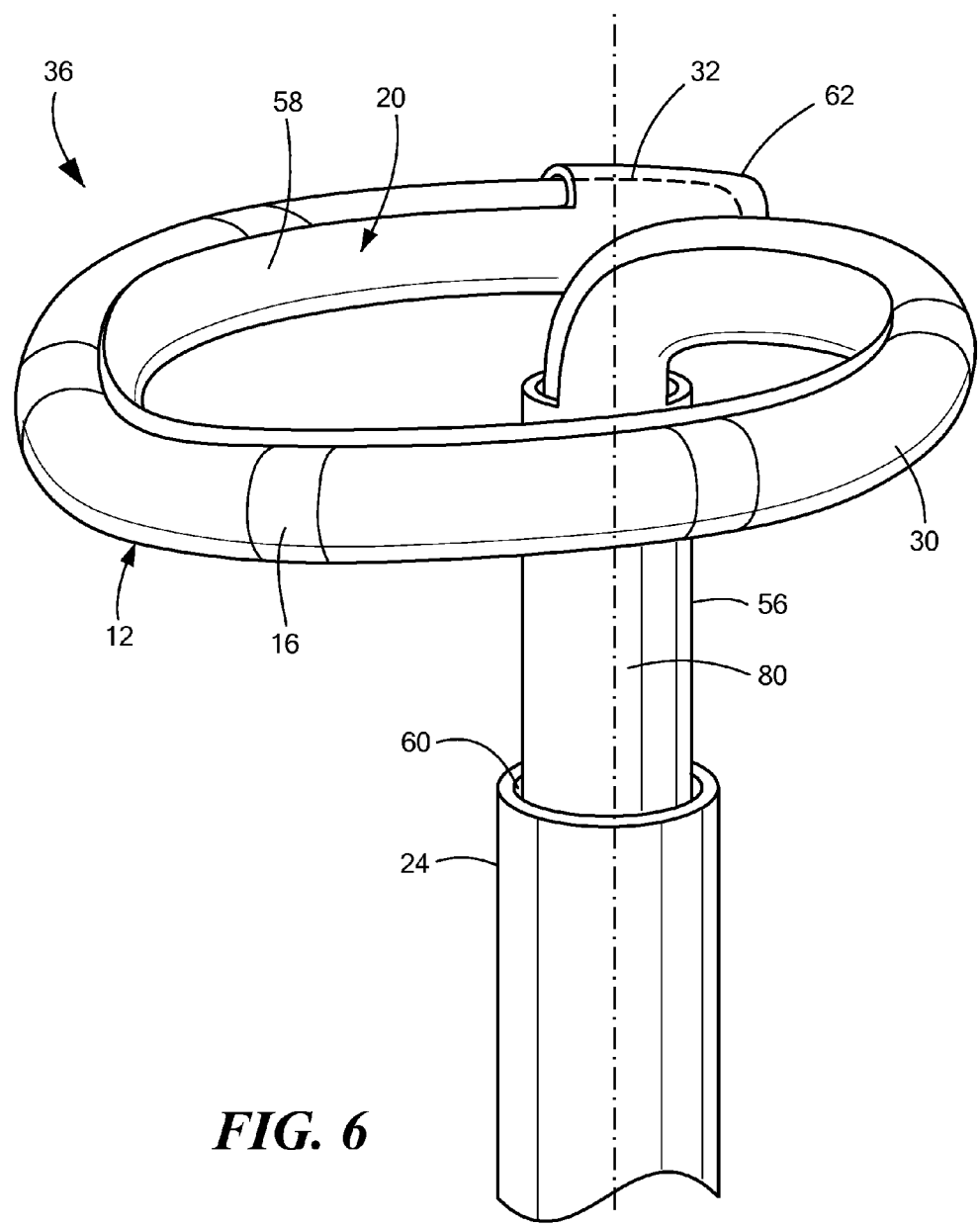
FIG. 6 shows a side view of a mapping catheter removably engaged within a support device.
Figure 7A:
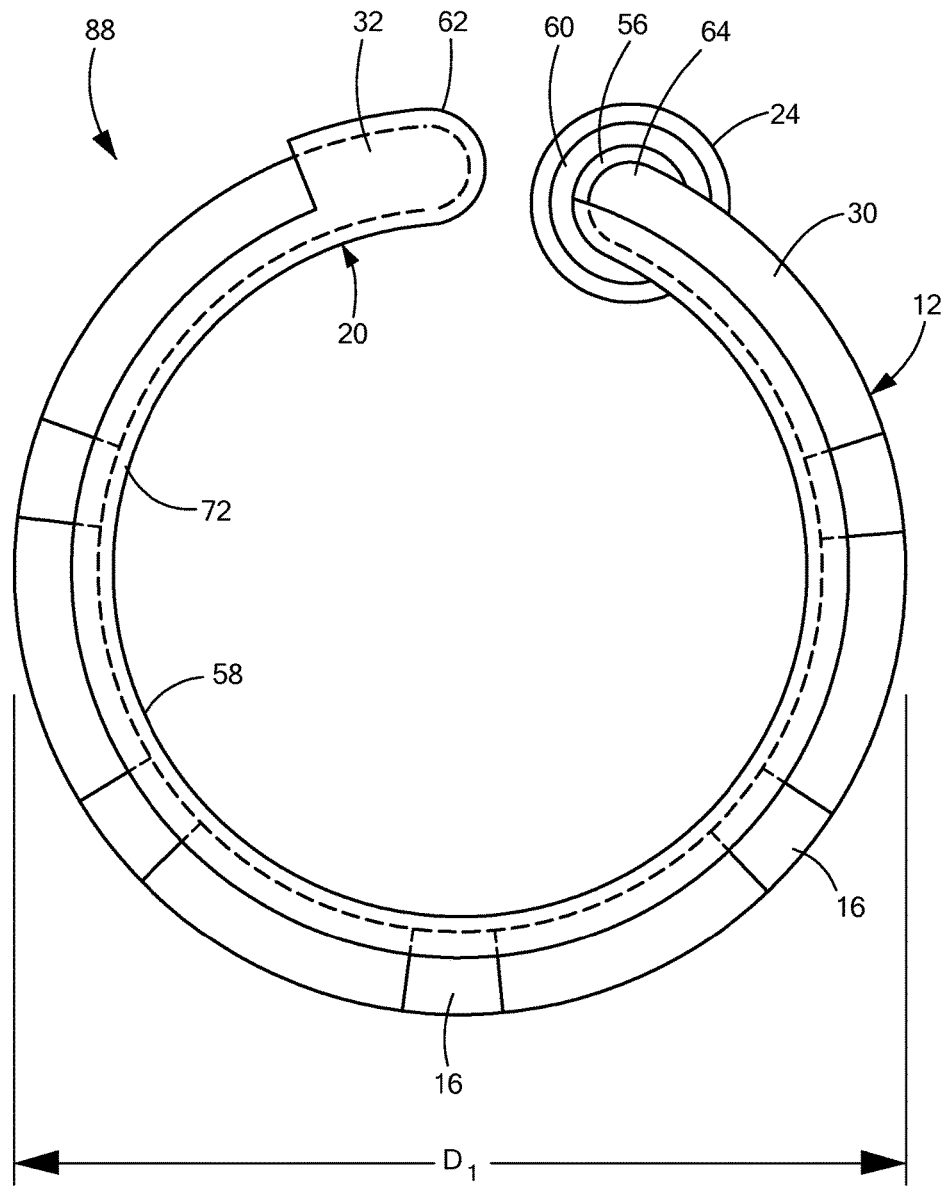
FIG. 7A shows a front view of a mapping catheter distal end removably engaged within a support device, the mapping catheter distal end and support device distal end having an arcuate shape with a first diameter.
Figure 7B:
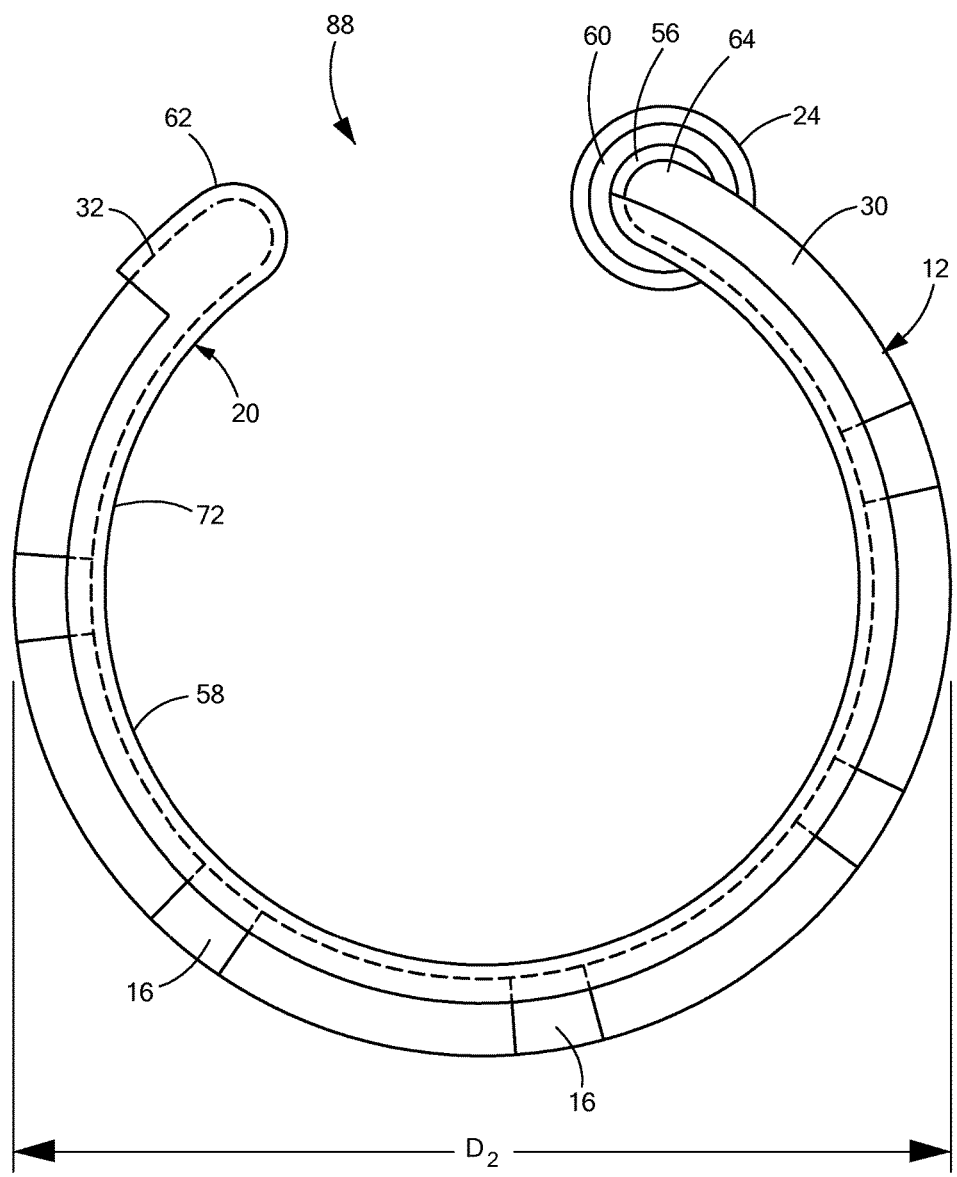
FIG. 7B shows a front view of a mapping catheter distal end removably engaged within a support device, the mapping catheter distal end and support device distal end having an arcuate shape with a second diameter.

Referring now to FIGS. 6-7B, a mapping catheter removably engaged within a support device is shown. Like the support device 20, the mapping catheter 12 may define a at least substantially linear first portion 80 and a second portion 30 that is transitionable between a first at least substantially linear configuration when the mapping catheter is within the support device and a second expanded configuration when the second portion 30 is passed out of the distal opening 84 of the closed lumen 22 of the proximal portion 56 of the support device 20. The second configuration may be arcuate, similar to the second expanded configuration of the distal portion 58 of the support device 20. When the support device 20 is in use, the first portion 80 of the mapping catheter 12 may be disposed within the closed lumen 22 of the proximal portion 56 of the support device 20. The distal portion 58 of the support device 20 may be sized to receive the second portion 30 of the mapping catheter 12. Further, the distal tip 32 of the mapping catheter 12 may be securely received within the closed lumen 22 of distal tip 62 of the support device 20. Thus, the second portion 30 of the mapping catheter 12 and the distal portion 58 of the support device 20 may transition between the first at least substantially linear configuration and the second expanded configuration together as a unit ("supported mapping catheter 36").

When the mapping catheter 12 is disposed within the support device 20, the exposed lumen 74 of the second portion 30 of the support device 20 may allow the one or more electrodes 16 located at the distal portion 58 of the mapping catheter 12 to remain exposed (that is, not covered or shielded by a portion of the wall 72 of the support device 20). In this way, the electrodes 16 may continue to record mapping signals and/or deliver pacing energy without being hampered or impeded by the support device 20.

The inner diameter Dsvc of the superior vena cava (SVC) may be larger than the inner diameter of, for example, a pulmonary vein ($D_{PV}$). Some mapping catheters such as the Achieve® Mapping Catheter (Medtronic, Inc., Minneapolis, Minn.) may have a distal portion that expands into an arcuate shape that is sized to be substantially in contact with an inner diameter of a pulmonary vein. However, the distal ends of such catheters may not be adequately sized to be substantially in contact with an inner diameter of the SVC.

Figure 7C:
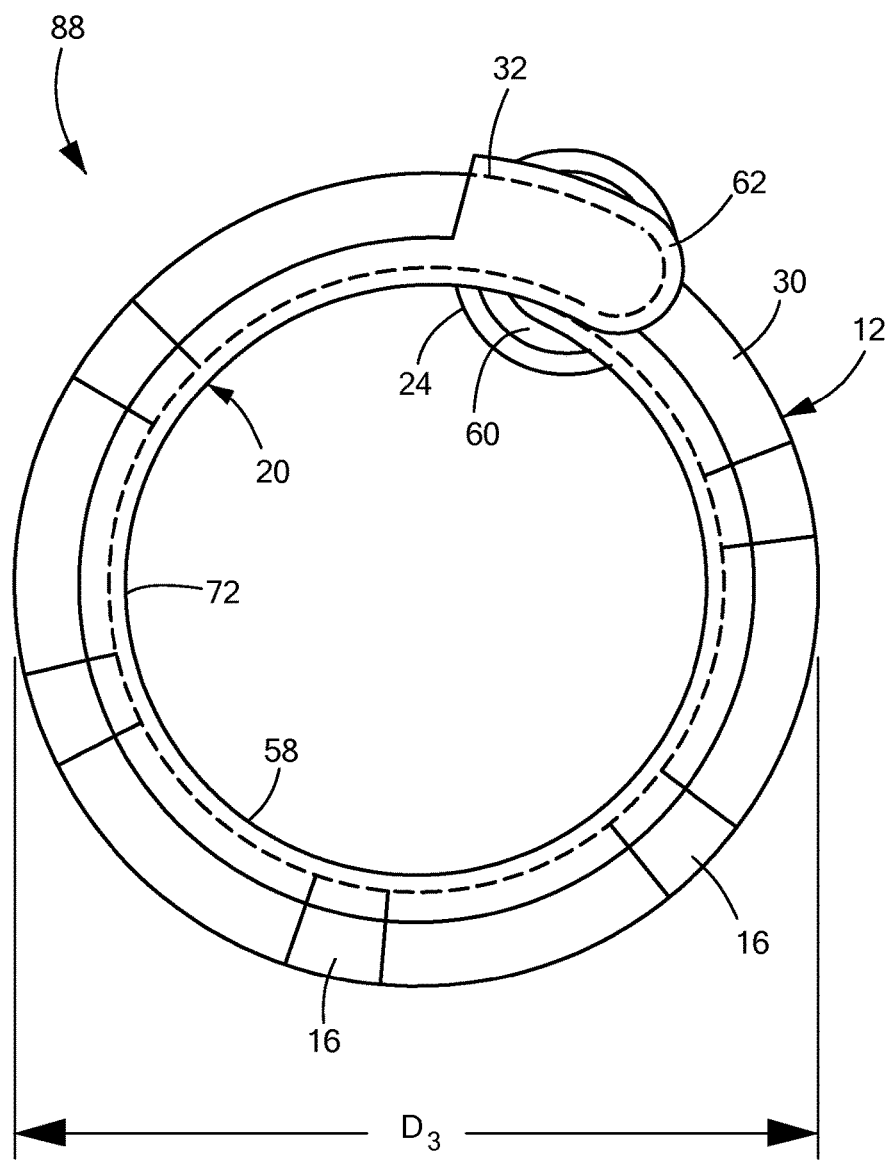
FIG. 7C shows a front view of a mapping catheter distal end removably engaged within a support device, the mapping catheter distal end and support device distal end having an arcuate shape with a third diameter.

As discussed above, the distal portion 58 of the support device 20 may be transitionable from a first at least substantially linear configuration to a second expanded configuration that has an arcuate shape. Further, the arcuate distal portion 58 may have a diameter that is adjustable to accommodate any of a variety of mapping and/or pacing targets. When the mapping catheter 12 is disposed within the support device 20, expansion of the distal portion 58 of the support device 20 may likewise expand the second portion 30 of the mapping catheter 12. The portion of wall 72 in the exposed lumen 74 and the wall 72 in the closed lumen of the support device distal tip 62 may ensure that the mapping catheter 12 remains securely disposed within the support device 20 as the diameter of the distal portion 58 of the support device 20 is increased or decreased. For example, the distal portion 58 may be expanded until the one or more electrodes 16 of the second portion 30 of the mapping catheter 12 are substantially in contact with an inner diameter of the SVC. In other words, the distal portion 88 of the supported mapping assembly 36 (that is, the support device 20 and mapping catheter 12 functioning together as a unit) may have an adjustable diameter to accommodate a range of vessel sizes. In a non-limiting example, the outer diameter of the distal portion 88 may be expanded from a first diameter $D_1$ (as shown in FIG. 7A) to a second diameter $D_2$ (as shown in FIG. 7B) or contracted to a third diameter $D_3$ (as shown in FIG. 7C). As the outer diameter of the distal portion 88 increases, the distance and angle $\alpha_3$ between the distal tip 62 and the starting point 64 of the arcuate portion may increase. Likewise, as the outer diameter of the distal portion 88 decreases, the distance and angle $\alpha_3$ between the distal tip 62 and the starting point 64 of the arcuate portion may decrease. In fact, the distance and angle $\alpha_3$ may decrease so much that the distal tip 62 may at least partially overlap the starting point 64 (as shown in FIG. 7C).

In order to adjust the diameter of the expanded distal portion 58 of the support device 20, and, consequently, the distal portion 88 of the supported mapping assembly 36, the support device 20 may include one or more actuator wires 68 each disposed in an enclosed channel 70 within the support device wall 72 (as shown in FIGS. 3A-3D). If one or more actuator wires 68 are used, the proximal portion 56 of the support device 20 may be composed of a material having a durometer that is great enough to resist bending, kinking, or otherwise being affected by a pull force exerted on the one or more actuator wires 68. That is, pulling the one or more actuator wires 68 may only affect the distal portion 58, and not the proximal portion 56, of the support device 20.

The one or more actuator wires 68 may be manipulated like pull wires. That is, a pull force may be exerted on the wires 68 to effect a change in the configuration and/or diameter of the distal portion 58 of the support device 20. For example, exerting a pull force on an actuator wire 68 located in a channel 70 disposed on an inner portion 72B of the support device wall 72 may cause the distal portion 58 of the support device 20 to transition from a at least substantially linear configuration to an expanded configuration, or may cause a decrease in the outer diameter of the distal portion 58 when in an expanded configuration. Similarly, exerting a pull force on an actuator wire 68 located in a channel 70 disposed on an outer portion 72A of the support device wall 72 may cause the distal portion 58 of the support device 20 to transition from an expanded configuration to a at least substantially linear configuration, or may cause an increase in the outer diameter of the distal portion 58 when in an expanded configuration.

Additionally or alternatively, the configuration and/or diameter of the distal portion 58 may be adjustable by using one or more actuator wires 68 that are composed of a shape-memory material, such as a metal alloy or polymer, that transitions from a first to a second configuration in response to a temperature change. For example, the one or more actuator wires 68 may be composed of a shape-memory material that has a neutral length at room temperature but contracts at increased temperatures (that is, temperatures beyond a predetermined transformation temperature), such as at the temperature of the surrounding blood and/or tissue when used in a medical procedure within a patient's body.

Additionally or alternatively, the configuration and/or diameter of the distal portion 58 may be adjustable by the transmission of an electrical charge through the one or more actuator wires 68. For example, the one or more actuator wires 68 may be composed of the shape-memory alloy FLEXINOL® (Dynalloy, Inc., Tustin, Calif.), which may contract with temperature increase beyond a predetermined transformation temperature. The transformation temperature may be between approximately 140° F. and approximately 230° F. (between approximately 60° C. and approximately 110° C.), which transformation temperature may be reached when an electrical charge is transmitted through the one or more actuator wires 68. The electrical charge may be generated by the electrical current source 55 and transmitted through each actuator wire 68, from a proximal portion to a distal portion, in order to heat the wire 68 to or beyond the transformation temperature. This heating may cause the wire 68 to contract, thus changing the configuration and/or diameter of the distal portion 58 of the support device 20. Once the transmission of electrical current through the wire 68 is stopped, the wire 68 may cool to a temperature below the transformation temperature and expand to a neutral length. As a non-limiting example, a FLEXINOL® actuator wire 68 may contract by several percent of its neutral length.

Electrical current may be transmitted to the one or more actuator wires 68 independently of electrical current transmitted to the one or more electrodes 16 of the mapping catheter, with a low baseline current being transmitted to the one or more actuator wires 68 during the entirety of a medical procedure. In contrast, pacing energy may be transmitted to the one or more electrodes 16 over a period of a few milliseconds (ms) every second. The system 10 may include a second electrical current source that is in communication with the one or more actuator wires 68, whereas a first electrical current source 55 may be in communication with the one or more electrodes 16 of the mapping catheter 12. Additionally or alternatively, a single electrical current source 55 may be used that is in communication with the one or more wires 68 and the one or more electrodes 16. In this case, the energy transmission may be modulated so that a constant low baseline current is transmitted to the one or more actuator wires 68 and a pacing signal is transmitted to the one or more electrodes 16 at the required intervals and at a level sufficient to excite, for example, the phrenic nerve.

Figure 8:
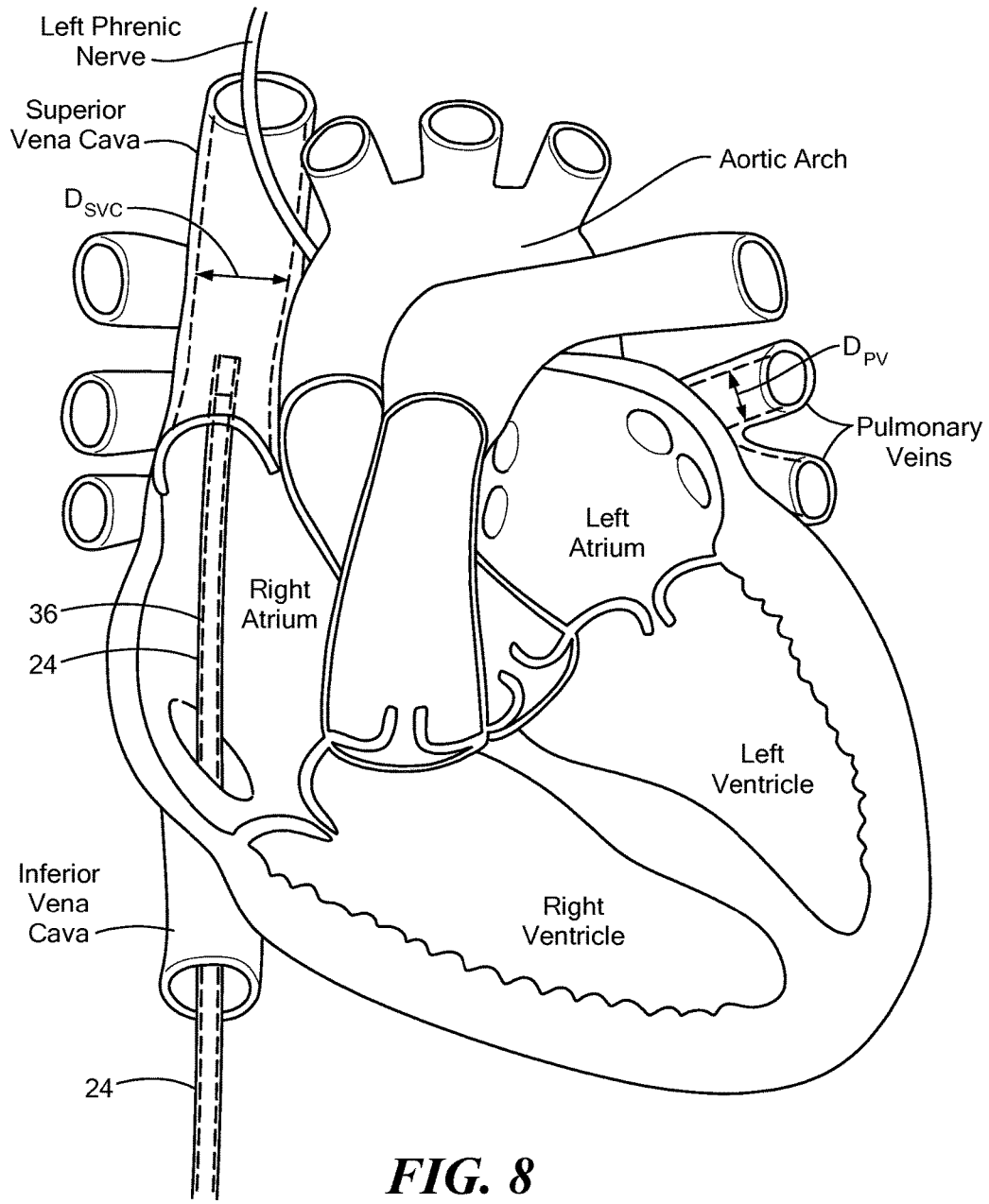
FIG. 8 shows a support device and mapping catheter located proximate the superior vena cava, the support device and mapping catheter being in a first delivery configuration.
Figure 9:
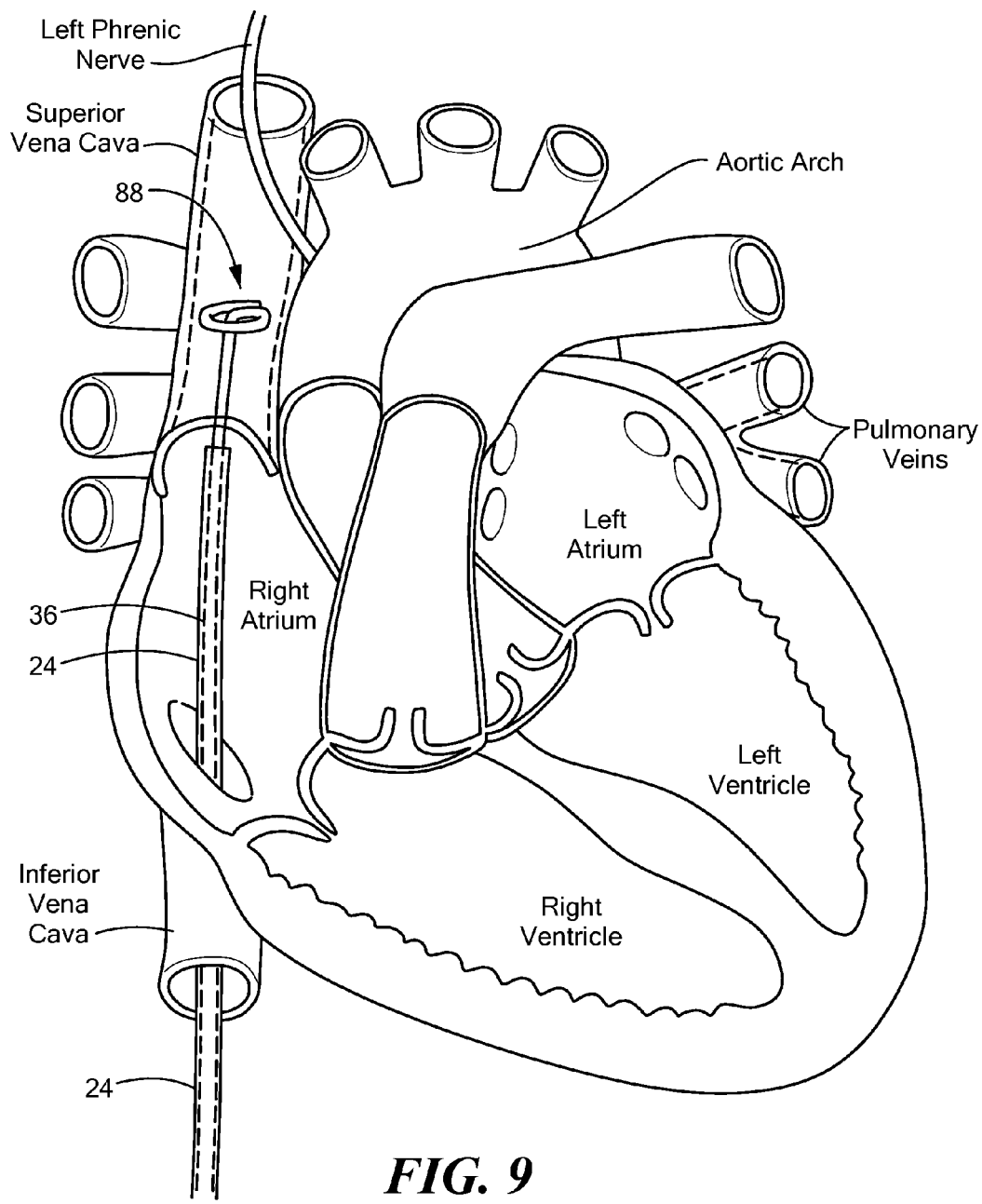
FIG. 9 shows a support device and mapping catheter located within the superior vena cava, the support device and mapping catheter being in a second expanded configuration, but not in contact with an inner diameter of the superior vena cava.
Figure 10:
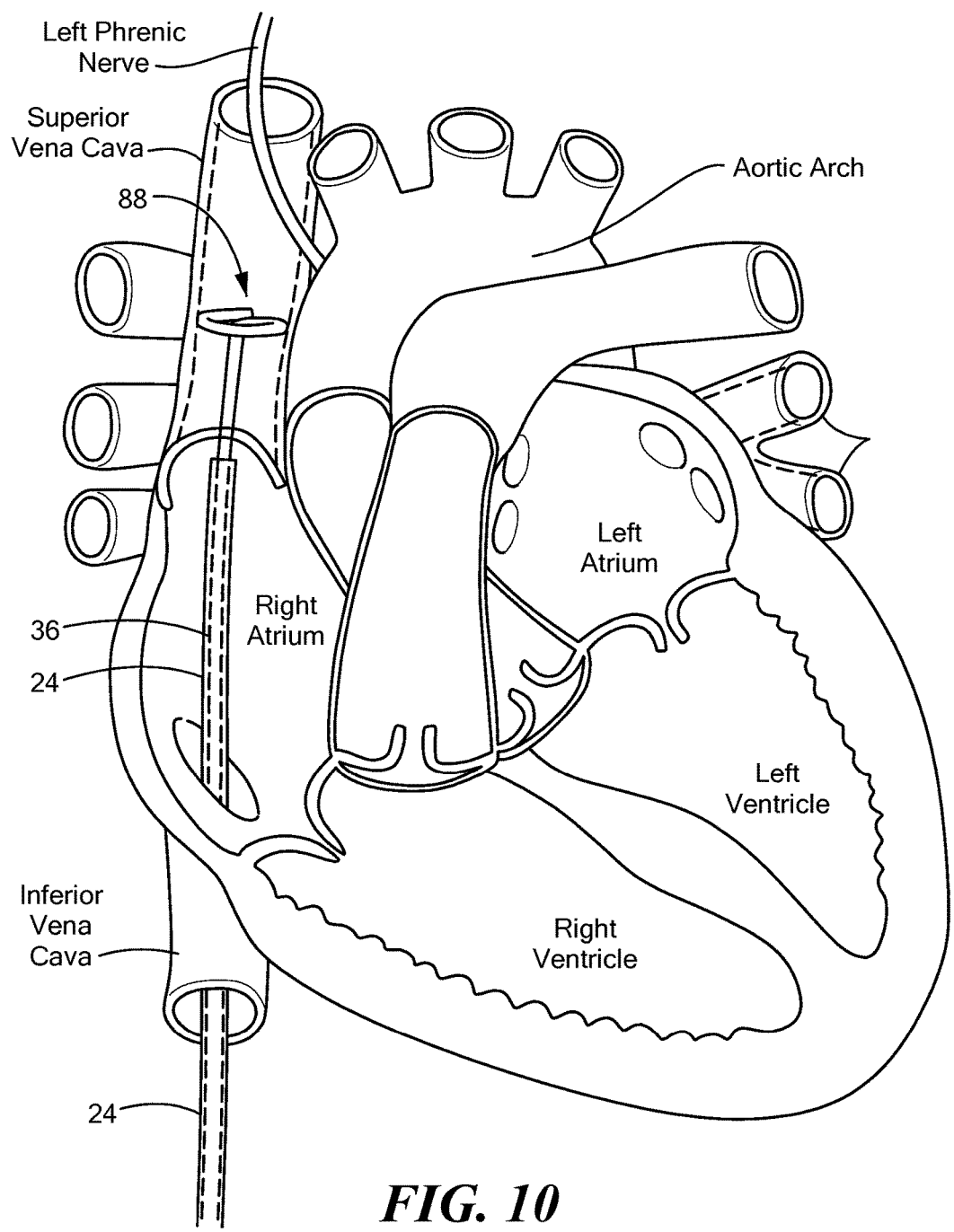
FIG. 10 shows a support device and mapping catheter located within the superior vena cava, the support device and mapping catheter being in a second expanded configuration.

Referring now to FIGS. 8-10, a method of using a supported mapping assembly 36 is shown. The supported mapping assembly 36 may be used to record mapping signals and/or deliver pacing energy to an area within a patient's cardiovascular system, such as the superior vena cava (SVC) during procedures to monitor the phrenic nerve during cryoablation within the heart for treatment of atrial fibrillation. As a non-limiting example of use, a sheath 24 may be advanced through the patient's vasculature to the right atrium of the heart. From the right atrium, the sheath 24 may be advanced a distance into the SVC to a target location that is proximate the phrenic nerve (FIG. 8).

Once the sheath 24 is near the target location, the support device 20, within which the mapping catheter 12 is engaged as shown and described in FIGS. 1-7B, may be advanced through the sheath 24 and out the distal opening 60. When the distal portion 88 of the supported mapping assembly 36 (that is, the support device 20 and mapping catheter 12 engaged therein) is within the sheath 24, the distal portions 58, 30 of the support device 20 and mapping catheter 12 may be in the first delivery or at least substantially linear configuration. When the distal portion 88 of the supported mapping assembly 36 is advanced beyond and out of the distal opening 60 of the sheath 24, the distal portions 58, 30 of the support device 20 and the mapping catheter 12 may be in the second expanded configuration having an arcuate shape (FIG. 9).

Initially, the distal portion 88 of the mapping assembly may have a first outer diameter $D_1$ (for example, as shown in FIG. 7A). However, the outer diameter $D_1$ may be smaller than the inner diameter $D_{svc}$ of the SVC and, therefore, the one or more electrodes 16 of the mapping catheter 12 may not be in contact with the SVC. To remedy this, the distal portion 88 of the supported mapping assembly 88 may be expanded to any outer diameter between the first outer diameter $D_1$ and a maximum possible outer diameter. For example, the distal portion 88 may be expanded from the first diameter $D_1$ to an enlarged second outer diameter $D_2$ that is sufficient to place the one or more electrodes 16 in contact with an interior circumference of the SVC at a location proximate a portion of the phrenic nerve, such as the left phrenic nerve (for example, as shown in FIGS. 7B and 10). Further, the distal portion 88 may be contracted from the first diameter $D_1$ or the second diameter $D_2$ to a third diameter $D_3$ for use in a vessel of the patient's vasculature that has, for example, an inner diameter that is less than that of a typical pulmonary vein. The expansion of the outer diameter of the distal portion 88 may be achieved using, for example, one or more actuator wires 68, as shown and described above. The distal portion 58 of the support device 20 may be stiffer or may have a higher durometer than that of the distal portion 82 of the mapping catheter 12. Thus, any adjustment or change in the configuration and/or diameter of the distal portion 58 of the support device 20 may cause the same change in the configuration and/or diameter of the distal portion 82 of the mapping catheter 12.

Although not shown, it will be understood that the same method shown and described in FIGS. 8-10 may also be used with a system that includes a treatment catheter 40, such as the system 10 shown and described in FIG. 2.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for monitoring a nerve proximate an ablation site, the system comprising:
 a support device defining a wall and including an at least substantially linear proximal portion of the support device having a length and a distal portion having a length and being transitionable between an at least substantially linear first configuration and an arcuate second configuration, the distal portion of the support device including a distal tip;
 the support device defining a lumen having a circumference and extending through the proximal portion and distal portion of the support device, the wall of the support device surrounding 360° of the lumen circumference along an entirety of the length of the proximal portion of the support device and the wall of the support device surrounding between 150° and 270° of the lumen circumference along an entirety of the length of the distal portion of the support device such that the wall defines an opening in the distal portion of the support device; and
 a mapping catheter within the lumen of the support device, the mapping catheter having an at least substantially linear proximal portion and a distal portion being transitionable between an at least substantially linear first configuration and an arcuate second configuration, the mapping catheter including at least one electrode on the distal portion thereof, the distal portion of the mapping catheter including a distal tip that is securely received within the distal tip of the support device to prevent movement of the mapping catheter within the support device when the mapping catheter is in use.

2. The system of claim 1, wherein the proximal portion of the support device defines a longitudinal axis and the distal portion of the support device lies in a plane that is substantially orthogonal to the longitudinal axis when the distal portion of the support device is in the arcuate second configuration.

3. The system of claim 1, wherein the proximal portion of the support device is composed of a first material having a first durometer and the distal portion of the support device is composed of a second material having a second durometer, the first durometer being greater than the second durometer.

4. The system of claim 1, wherein the distal portion of the support device in the arcuate second configuration has an adjustable outer diameter.

5. The system of claim 1, wherein the proximal portion of the mapping catheter is disposed within the lumen in the proximal portion of the support device and the distal portion of the mapping catheter is disposed within the lumen in the distal portion of the support device.

6. The system of claim 5, wherein at least a portion of each of the at least one electrode on the distal portion of the mapping catheter is exposed through the opening in the wall in the distal portion of the support device.

7. The system of claim 6, wherein the distal portion of the support device in the arcuate second configuration has an adjustable diameter that is transitionable between a first outer diameter and a second outer diameter.

8. The system of claim 7, further comprising an energy source in electrical communication with the at least one electrode of the mapping catheter.

9. The system of claim 8, wherein the support device further includes at least one actuator wire, the at least one actuator wire including a distal portion that is coupled to the distal portion of the support device.

10. The system of claim 9, wherein the at least one actuator wire is in communication with the energy source.

11. The system of claim 10, wherein the distal portion of the support device is transitioned between the first and second outer diameters when an electrical current from the energy source is transmitted through the at least one actuator wire.

12. The system of claim 9, wherein the support device wall defines an enclosed channel, the at least one actuator wire being disposed within the enclosed channel.

13. The system of claim 12, wherein the outer diameter of the distal portion of the support device in the arcuate second configuration is adjusted by manipulating the at least one actuator wire.

14. The system of claim 13, wherein manipulating the at least one actuator wire includes at least one action selected from the group consisting of heating the at least one actuator wire to a temperature greater than a predetermined transformation temperature and exerting a pull force on the at least one actuator wire.

15. A support device sized and configured to be used with a mapping catheter, the support device comprising:
   an elongate body defining a wall with at least one enclosed channel and including an at least substantially linear proximal portion having a length and defining a longitudinal axis and a distal portion having a length and being transitionable between an at least substantially linear first configuration and expanded second configuration, the distal portion including a distal tip; and
   at least one actuator wire within the at least one enclosed channel in the wall of the elongate body, the at least one actuator wire including a distal portion coupled to the distal portion of the elongate body and a proximal portion couplable to an actuator mechanism,
   the elongate body defining a lumen having a circumference and extending through the proximal portion and distal portion of the elongate body, the lumen being sized to receive the mapping catheter therein, the wall of the elongate body surrounding 360° of the lumen circumference along an entirety of the length of the proximal portion of the elongate body and the wall of the elongate body surrounding between 150° and 270° of the lumen circumference along the length of the distal portion of the elongate body,
   the distal portion of the elongate body in the second expanded configuration having an adjustable diameter that is transitionable between a first outer diameter and a second outer diameter by actuation of the at least one actuator wire,
   the distal tip of the elongate body being configured to removably engage the mapping catheter and to prevent movement of the mapping catheter within the support device when the mapping catheter is in use.

16. The support device of claim 15, wherein the distal portion of the elongate body lies in a plane that is substantially orthogonal to the longitudinal axis of the proximal portion of the elongate body when the distal portion of the elongate body is in the second expanded configuration.

17. The support device of claim 15, wherein the proximal portion of the elongate body is composed of a first material having a first durometer and the distal portion of the elongate body is composed of a second material having a second durometer, the first durometer being greater than the second durometer.

* * * * *